United States Patent [19]

Johnson et al.

[11] Patent Number: 4,637,818

[45] Date of Patent: Jan. 20, 1987

[54] APPARATUS FOR PRODUCING STERILITY IN FEMALE ANIMALS

[76] Inventors: Richard K. Johnson, 20656 View Oaks Way, San Jose, Calif. 95120; John W. Algeo, P.O. Box 158, Templeton, Calif. 93465

[21] Appl. No.: 799,316

[22] Filed: Nov. 18, 1985

Related U.S. Application Data

[62] Division of Ser. No. 555,063, Nov. 23, 1983.

[51] Int. Cl.$^4$ .............................................. A61M 5/18
[52] U.S. Cl. ..................................... 604/89; 604/237; 604/55; 417/550
[58] Field of Search ............................ 604/89–91, 604/237, 55, 56; 417/550

[56] References Cited

U.S. PATENT DOCUMENTS

| Re. 29,207 | 5/1977 | Bolduc et al. | 128/235 |
|---|---|---|---|
| 2,984,190 | 5/1961 | Dibley et al. | 417/550 X |
| 3,042,030 | 7/1962 | Read | 128/127 |
| 3,511,239 | 5/1970 | Tuschoff | 604/89 |
| 3,699,961 | 10/1972 | Szpur | 604/89 |
| 3,707,146 | 12/1972 | Cook et al. | 604/96 X |
| 3,805,767 | 4/1974 | Erb | 128/1 R |
| 3,822,702 | 7/1974 | Bolduc | 128/235 |
| 3,875,939 | 4/1975 | Bolduc et al. | 128/235 |
| 4,119,098 | 10/1978 | Bolduc et al. | 128/235 |
| 4,160,446 | 7/1979 | Barrington | 128/1 R |

FOREIGN PATENT DOCUMENTS

| 1470573 | 3/1974 | United Kingdom . |
| 1430045 | 3/1976 | United Kingdom . |
| 2021956 | 12/1979 | United Kingdom . |

OTHER PUBLICATIONS

Text on Pumps, pp. 166 and 167–published more than one year prior to the filing date of parent application.

*Primary Examiner*—Dalton L. Truluck
*Attorney, Agent, or Firm*—Jack M. Wiseman

[57] ABSTRACT

Apparatus for injecting flowable material in which a container holds flowable material. Disposed within the container is a plunger which is formed with metering apertures extending therethrough. The metering apertures store predetermined quantities of material to be mixed with the material in the container. A flexible member is disposed adjacent the plunger between the discharge opening of the container and the plunger. When the plunger travels away from the discharge opening, the flexible member unseals the metering apertures for mixing the material in the plunger with the material in the container. When the plunger travels toward the discharge opening, the flexible member seals the metering apertures in the plunger to discharge the mixed material in the container through the discharge opening.

7 Claims, 2 Drawing Figures

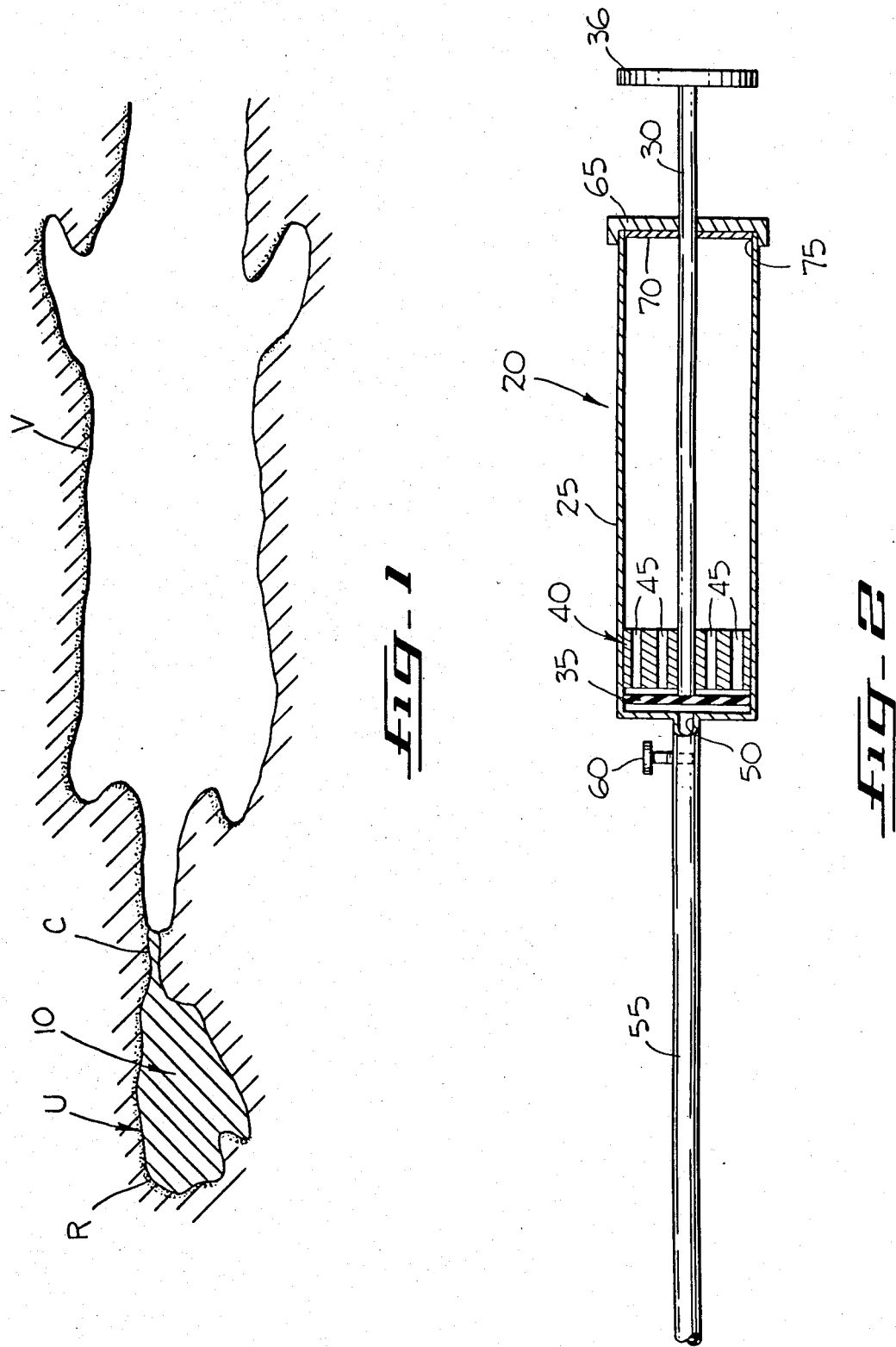

dcr has a wide base to serve as an obturator. The powder dissolves upon use.

APPARATUS FOR PRODUCING STERILITY IN FEMALE ANIMALS

This application is a division of our pending application, Ser. No. 555,063, filed on Nov. 23, 1983, for Method Of Producing Sterility In Female Animals.

BACKGROUND OF THE INVENTION

The present invention relates in general to a method of producing sterility in female animals, and more particularly to a method of producing sterility in female animals by an obturator implanted in the uterus of a female animal.

Cattle are customarily fattened before being slaughtered. Many different techniques have been employed such as controlling the intake of feed and controlling the type of feed consumed by the cattle.

Some cattle have been fed various drugs and chemicals to increase the weight thereof before being slaughtered. A melengestrol acetate and a progestogen have been fed to heifers to depress the estrus cycle and thereby cause a cessation of heat periods. As a consequence thereof, the body weight of the heifers is increased and the efficiency in food consumption fattens the heifers. However, this technique requires accurate dispensing of the drug on a daily basis and the heifer subjected to the drug cannot be slaughtered within 48 hours of the last administration of the drug.

Hormone implants have been used to fatten heifers for beef. The hormone implants can be discarded with the inedible parts of the carcass and thus obviate the need to feed daily a chemical or to withdraw the heifer prior to slaughter.

Dromostanolene propinate in pellet form has been implanted subcutaneously in a heifer to increase the weight thereof. The estrus cycle of the heifer is suppressed.

In an article entitled OPERATIVE CORRECTION OF PARTIAL EPIPHYSEAL PLATE CLOSURE BY OSSEOUS-BRIDGE RESECTION AND SILICANE-RUBBER IMPLANT by Robert W. Bright, appearing in *The Journal Of Bone And Joint Surgery*, American Volume, Volume 56-A, No. 4, June 1974, pp. 655–664, there is described an experimental study on dogs. A procedure is discussed in which silicone-rubber material is molded to fill an osseous defect. The material is applied and allowed to vulcanize.

Silicone elastomer has been used for sterilization of human females by injection into the fallopian tubes. The injected material is in a liquid state and subsequently vulcanizes to form a plug.

The patent to Dickinson, III, et al., U.S. Pat. No. 3,811,424, discloses a method of inserting a mechanical device, which clamps around the annulus of a cow's cervix. For this purpose, a clamping ring slides over and compresses against the projecting annulus of the cow's cervix. The method alters the cross-sectional configuration of the reproductive tract with subsequent stimulation and changing (or resetting) of the estrus cycle.

In the patent to Robinson, U.S. Pat. No. 3,916,898, there is disclosed a method of controlling estrus, ovulation and fertility in domestic animals by introducing into the vagina, and later removing, a sponge impregnated with a progestational compound. The patent to Haller, U.S. Pat. No. 3,690,316, discloses a cervical obturator for humans, which is made of a compressed spermicidal powder in the shape of fusiform. The powder dissolves upon use.

The patent to Vennard et al., U.S. Pat. No. 3,779,241, discloses a preformed hollow body having thin, flexible walls which have the size and shape of the uterine cavity. A flexible, compressible, filler material fills the hollow body, whereby the walls of the hollow body will make contact with the walls of the uterine cavity. The filler material is polymerizable organosiloxane material. The patent to Bolduc et al., U.S. Pat. No. 4,119,098, discloses a dispensing apparatus for placing settable material in the uterine cavity and moving the material from the uterine cavity into the Fallopian tubes. It seals the cervical entrance to the cavity and causes expansion to conform to the slope of the uterine cavity and force the dispensed materials into the canals of the Fallopian tubes.

In the patent to Barrington, U.S. Pat. No. 4,160,446, there is disclosed a device to deliver a tubal-occluding polymer such as organosilicon rubber. The material is a foamable polymer that flows into the Fallopian tubes to occlude the tubes.

The patent to Erb, U.S. Pat. No. Re. 29,345, discloses a method for the sterilization of humans, in which a removable tip is inserted into the uterus. The tip is aligned with the uterine end of the oviduct. A curable elastomeric composition is injected through the tip into the oviduct to fill the oviduct adjacent to the uterus. The elastomer composition solidifies on the tip. The apparatus for inserting the tip in the uterus is removed and the tip is ejected by the apparatus to remain for blocking the oviduct. The apparatus is inserted through the cervical os into the uterus. The material used is silicon elastomers.

In the patent to Chvapil, U.S. Pat. No. 4,274,410, a collagen porous sponge is inserted in the upper vault of the vagina near the cervix. The sponge is preformed before it is inserted in the upper vault of the vagina near the cervix. In the patent to Chvapil, U.S. Pat. No. 4,369,773, there is disclosed a preformed collagen sponge inserted into the upper vault of the vagina to cover the cervix.

The patent to Brundin, U.S. Pat. No. 4,365,621, discloses a device for blocking the oviduct which includes a body made of hydrogels. The body swells by absorbing body fluids. The body is introduced into a cavity in its normal state and enlarges upon the absorption of body fluid to block a passage or close a cavity.

In the patent to Vickery, U.S. Pat. No. 3,991,750, issued on Nov. 16, 1976, for Dromostanolene Propinate Implant Pellet Useful For Producing Weight Gains In Animals And Suppressing Estrus In Female Animals, there is described the implant of a pellet subcutaneously in a heifer. The pellet contains dromostanolene propinate and produces an increase in weight in the heifers and suppresses the estrus cycle in the heifer.

SUMMARY OF THE INVENTION

A flowable material is injected into the uterus of a female animal, which expands and is cured at body temperature to implant an obturator in the uterus of the female animal for producing sterility in the female animal.

An obturator made of a collagen compound or a silicone elastomer is used as a progestogen to depress the estrus cycle in the female animal. This action causes a cessation of heat periods and results in improved body weight gains and results in more efficient utilization of feed consumed by the female animal. Thus, the female animal is fattened for slaughter in the production of beef.

An object of the present invention is to produce sterility in a heifer by intrauterine injection of flow material, such as a silicone elastomer or a collagen compound for implanting in the cervical os of the uterus of the heifer a permanent obturator. The flowable material is expanded and cured by the body heat of the heifer. The implant of the obturator in the cervical os of the uterus of the heifer serves to maintain through the course of the feed lot period for the heifer a weight gain, which is greater than average weight gain heretofore realized during the feed lot period.

By virtue of an intrauterine injection of flowable material, the problem of proper mechanical size for the obturator is obviated. A mechanical obturator of a wrong size for the female animal may require further instruments. Mechanical obturators are difficult to install.

Implanting or manipulating the reproductive organs of a female animal other than the uterus may require operative procedures with all attendant risks. This problem has also been obviated by the present invention since the flowable material is injected through the vagina into the uterus.

BRIEF DESCRIPTION OF THE DRAWINGS

FIG. 1 is a fragmentary, diagrammatic illustration of an obturator made of a silicone elastomer or a collagen compound implanted in the uterus of a heifer in accordance with the present invention.

FIG. 2 is a fragmentary, diagrammatic axial sectional view of a material injecting device employed in the present invention for implanting an obturator in the uterus of a heifer.

DETAILED DESCRIPTION OF THE PREFERRED EMBODIMENTS

Illustrated in FIG. 1 is a diagrammatic sectional view of reproductive organs of a heifer, which includes a vagina V, a cervical os C of a uterus U, and a cornu R of the uterus U. Implanted in the cervical os C of the uterus U and in at least one cornu R of the uterus U is an obturator 10 made of a silicone elastomer or a collagen compound. The obturator 10 is permanently implanted in the uterus U.

For implanting the obturator 10 in the uterus U, a suitable material injecting device 20 (FIG. 2) is employed. The material injecting device 20, in the exemplary embodiment, comprises a cylinder 25. Disposed within the cylinder 25 for reciprocating movement is a piston rod 30. Adjacent one end of the piston rod 30 is a thin disc 25 made of rubber. At the other end of the piston rod 30 is a suitable handle 36.

Fixed to the piston rod 30 adjacent to the disc 35 is a plunger 40. The disc 35 is axially aligned with the plunger 40. The plunger 40 is formed with a plurality of axially disposed apertures 45 that extend therethrough. Disposed within the apertures 45 of the plunger 40 is a prescribed or metered amount of a catalyst of the flow material hardening into the obturator 10. A suitable parting material is disposed in the apertures 45 of the plunger 40 at the end thereof toward the handle 36.

At one end of the cylinder 25 is a discharge opening 50, which communicates with a suitable discharge tube 55. The tube 55 may be made of flexible rubber or plastic material. It may also be made of stainless steel. A stop-cock 60 disposed in the tube 55 opens and closes the axial opening of the tube 55 in a conventional manner.

At the other end of the cylinder 25 is a suitable removable cap 65 within which is disposed a gasket 70. The cap 65, when mounted on the cylinder 25, provides a sealed end therefor. Initially, the stop-cock 60 is in the closed position and the cap 65 is removed from the cylinder 25. Initially, the piston 35 and the plunger 40 are disposed at the end of the cylinder 25 adjacent the discharge opening 50. The plunger 40 has previously been filled with a predetermined quantity of a catalyst and also with the parting material. A base of the flowable material that is cured by body heat to form the obturator 10 is deposited in the cylinder 25 through an opening 75. The base of the flowable material is disposed between the plunger 40 and the opening 75. Now, the cap 65 with the gasket 70 is securely attached to the cylinder 25 to form a seal.

The piston rod 30 is actuated to move the plunger 40 and the disc 35 toward the cap 65. The plunger 40 during this operation is pulled through the base of the flexible material, and the base of the flowable material is thereby mixed with the catalyst and parting material in the cylinder 25. The disc 35 is displaced away from the apertures 45 at the adjacent end of the plunger 40 during the mixing operation in the cylinder 25 to open or unseal the ends of the apertures 45 at the end of the plunger 40 facing the discharge opening 50. The plunger 40 at the end of the mixing operation is adjacent the gasket 70. Now the stop-cock is opened and the piston rod 30 is now actuated to move toward the discharge opening 50. The flowable material is ejected by the plunger 40 from the cylinder 25 through the free end of the tube 55. The disc 35 is moved away from the apertures 45 and assumes a concave-convex configuration to unseal the same at the adjacent end of the plunger 40 during the mixing of the base of the flowable material and the catalyst. While the flowable material is being ejected from the cylinder 25 by the plunger 40, the disc 35 forms a seal for the apertures 45 by engaging the adjacent end of the plunger 40 to enable the flowable material to be ejected by the plunger 40 from the cylinder 25.

For injecting the flowable material into the uterus U of a cow or a heifer, the cow or heifer is manipulated transvaginally. The tube 55 is passed through the vagina V and inserted into the os of the cervix C of the uterus U. The flowable material passes into the cervix C of the uterus U and optionally may also pass into one or more cornu of the uterus U. If desired, the flowable material may additionally pass into the corpus of the uterus U. Thus, an intrauterine injection of flowable material is performed and the tube 55 passes into the cervix C of the uterus U. The intrauterine injection of the flowable material should be performed while the cow or heifer is confined by a squeeze gate or chute for cattle.

The flowable material may be in a liquid state or in a foam state. One suitable flowable material is an elastomer of silicone material, which vulcanizes or cures at the body temperature of a cow or heifer. Such a silicone elastomer is sold by Dow Corning Corporation as Silastic 382 Medical Grade Elastomer. The Silastic 382 Medical Grade Elastomer comprises an elastomer base of polydimethylsiloxane and silica filler as one liquid and a liquid catalyst of stannous octoate. The liquid catalyst of stannous octoate is sold by Dow Corning Corporation as Dow Corning Catalyst M. A suitable bonding agent or adhesive employed with the flowable material of silicone elastomer is a Dow Corporation Silastic Medical Adhesive Silicone A.

The catalyst and the bonding agent are disposed in the holes 45 of the plunger 40. The elastomer base of polydimethylsiloxane and silicone filler are disposed in the cylinder 25 between the plunger 40 and the opening 70. The flowable material comprises 0.5 parts of the catalyst to 100 parts of the elastomer base by volume. The flowable material is expanded and cured in the uterus U at the body temperature of the cow or heifer to implant the obturator 10 in the uterus U. The implant of the obturator 10 is in the cervical canal or os C of the uterus U and also in one or more cornu R of the uterus U. The minimum time required for the curing of the flowable material to implant the obturator 10 in the uterus U is 5 minutes. To implant the obturator 10 in a heifer between 10 cc and 30 cc of flowable material is used.

Another suitable flow material is a silicone foam elastomer which vulcanizes or cures at the body temperature of a cow or heifer. Such a silicone foam elastomer is sold by Dow Corning Corporation as Dow Corning DT-4290 Prosthetic Foam. The Dow Corning DT-4290 Prosthetic Foam comprises a silicone foam elastomer base mixture of polydimethylsiloxane and polymethylhydrogensiloxane. The catalyst used with the silicone foam elastomer is stannous octoate, which is sold by Dow Corning Corporation as Dow Corning Q7-4290 catalyst. The flow material is produced by six parts of Dow Corning Q7-4290 catalyst with 100 parts of Dow Corning silicone foam elastomer base by weight.

The catalyst is disposed in the holes 45 of the plunger 40. The silicone foam elastomer base is disposed in the cylinder 25 between the plunger 40 and the opening 70. The flowable material is expanded and cured in the uterus U at the body temperature of the cow or heifer to implant the obturator 10 in the uterus U. The implant of the obturator 10 is in the cervical canal or os C of the uterus U and also in one or more cornu R of the uterus U.

The minimum time required for the curing of the flowable material to implant the obturator 10 in the uterus U is 2 minutes.

To implant the obturator 10 in a heifer between 5 cc and 10 cc of flowable material is used.

Another suitable flow material is a collagen material of the type used in plastic surgery and by dermatologists. Such collagen material has been supplied by Collagen Corporation of Palo Alto, Calif. For example, Collagen Corporation supplies a ZYDERM collagen composed of highly purified bovine dermal collagen in physiological saline or a highly purified form of collagen made from calf hide in physiological saline. Between 20 cc and 30 cc of the collagen material which was buffered with a saline dilutant is injected into the uterus U of a heifer. The collagen material expands and cures at the body temperature of a heifer. Fifty-five minutes after the injection of the collagen material into a heifer, the collagen material solidifies sufficiently to implant in the uterus U of a heifer the obturator 10. The obturator 10 is implanted in the cervical canal or os C of the uterus U, the cornu R of the uterus U and in the corpus of the uterus U. The injection of the collagen material in the uterus U of a heifer can be carried out with the same material injecting device as used for the silicone elastomer.

We claim:

1. Apparatus for injecting flowable material comprising:
    (a) a cylinder, said cylinder being formed with a discharge opening at one end thereof;
    (b) a piston rod disposed in said cylinder, said piston rod being movable over a rectilinear path in said cylinder, said piston rod at one end section thereof projecting out of said cylinder;
    (c) a flexible member disposed in said cylinder and secured to said piston rod at the other end section thereto for movement therewith;
    (d) a plunger disposed in said cylinder and secured to said piston rod for movement therewith, said plunger being disposed adjacent said flexible member between said flexible member and said one end section of said piston rod,
    (e) said plunger, said flexible member and said piston rod being arranged coaxially, said plunger being formed with a plurality of axially disposed metering apertures therethrough, said metering apertures containing predetermined quantities of material to be mixed within said cylinder;
    (f) a sealing lid separately attached to said cylinder at the other end thereof and formed with a central opening to receive said piston rod for reciprocating movement over said rectilinear path, said cylinder being arranged to contain flowable material insertable into said cylinder at the other end thereof; and
    (g) a handle attached to said one end section of said piston rod projecting out of said cylinder for imparting a reciprocating movement to said piston rod over said rectilinear path, the movement of said piston rod away from said discharge opening causes said flexible member to flex in one direction for unsealing said metering apertures in said plunger at the end thereof adjacent said flexible member for the mixing of the material in said metering apertures of said plunger with the flowable material in said cylinder as said piston rod travels away from said discharge opening, and the movement of said piston rod toward said discharge opening causes said flexible member to flex in an opposite direction for sealing said metering apertures in said plunger at the end thereof adjacent said flexible member to urge said mixed material in said cylinder to be discharged through said discharge opening during the travel of said piston rod by the urging action of said plunger and said flexible disc.

2. Apparatus according to claim 1, and comprising a discharge tube communicating with said discharge opening for receiving mixed material contained in said cylinder; and means on said discharge tube for controlling the passage of material through said discharge tube, said means stopping the passage of material through said discharge tube while said piston rod is travelling away from said discharge opening and said means enabling the passage of material through said discharge tube while said piston rod is travelling toward said discharge opening.

3. Apparatus according to claim 1 wherein said plunger has a cylindrical configuration and is dimensioned to slidingly engage the inner cylindrical wall of said cylinder.

4. Apparatus according to claim 2 wherein said plunger has a cylindrical configuration and is dimensioned to slidingly engage the inner cylindrical wall of said cylinder.

5. Apparatus according to claim 3 wherein said flexible member has a disc shape.

6. Apparatus according to claim 4 wherein said flexible member has a disc shape.

7. Apparatus for injecting flowable material comprising:
  (a) a container adapted to contain flowable material, said container being formed with a discharge opening;
  (b) a plunger disposed in said container, said plunger being formed with a plurality of metering apertures extending therethrough, said metering apertures containing predetermined quantities of material to be mixed;
  (c) means for moving said plunger in a reciprocal movement, said metering apertures of said plunger extending in the direction of travel of said plunger; and
  (d) a flexible member disposed adjacent said plunger between said discharge opening and said plunger, said flexible member being arranged to unseal said metering apertures in said plunger while said plunger travels away from said discharge opening for mixing the material in said plunger with the material in said container, said flexible member being arranged to seal said metering apertures in said plunger while said plunger travels toward said discharge opening to discharge mixed material in said container through said discharge opening.

* * * * *

UNITED STATES PATENT OFFICE
CERTIFICATE OF CORRECTION

Patent No. 4,637,818                  Dated January 20, 1987

Inventor(s) RICHARD K. JOHNSON

It is certified that error appears in the above-identified patent and that said Letters Patent are hereby corrected as shown below:

Line 2 of face sheet, delete "et al."

Item [76] of face sheet, delete "John W. Algeo, P.O. Box 158, Templeton, Calif. 93465"

Column 5, line 67, change "we" to ---I---.

Signed and Sealed this

Twenty-fourth Day of March, 1987

*Attest:*

*Attesting Officer*

DONALD J. QUIGG

*Commissioner of Patents and Trademarks*